United States Patent [19]

Karaki et al.

[11] Patent Number: 4,706,185
[45] Date of Patent: Nov. 10, 1987

[54] APPARATUS FOR DISPLAYING ULTRASONIC IMAGE

[75] Inventors: Kouichi Karaki, Hino; Fumio Uchino, Hachioji, both of Japan

[73] Assignee: Olympus Optical Co., Ltd., Japan

[21] Appl. No.: 859,926

[22] Filed: May 5, 1986

[30] Foreign Application Priority Data

May 14, 1985 [JP] Japan .................................. 60-102042

[51] Int. Cl.$^4$ .......................... G01S 9/68; G01N 29/04
[52] U.S. Cl. ...................................... 367/110; 73/618
[58] Field of Search .................. 367/110; 73/596, 597, 73/598, 607, 618, 619, 620, 621

[56] References Cited

U.S. PATENT DOCUMENTS 3,918,025 11/1975 Koshikawa et al. ................ 367/110
4,541,281 9/1985 Chubachi et al. .................... 73/619
4,596,145 6/1986 Smith et al. ........................... 73/607

FOREIGN PATENT DOCUMENTS 0128692 10/1979 Japan ................................... 367/110

Primary Examiner—Stephen C. Buczinski
Assistant Examiner—Melissa Koltak
Attorney, Agent, or Firm—Parkhurst & Oliff

[57] ABSTRACT

An apparatus for displaying ultrasonic images picked-up by an ultrasonic microscope including a digital scan converter having three image memories for storing successively picked-up three ultrasonic images. The digital scan converter functions to reconstruct a color image from the three ultrasonic images by simultaneously reading ultrasonic image signals out of the image memories as red, green and blue color signals.

6 Claims, 6 Drawing Figures

FIG_2

FIG_5
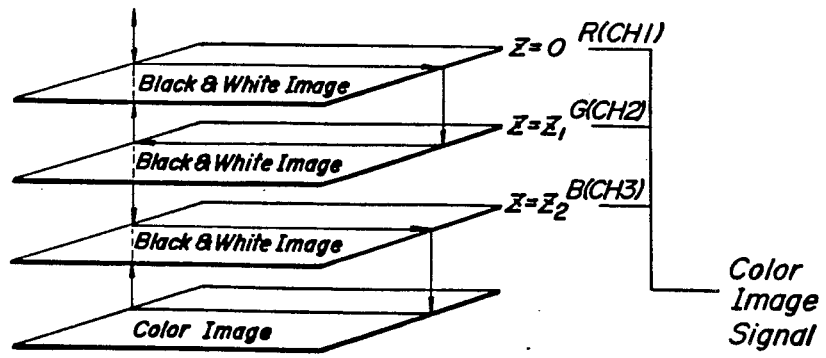

APPARATUS FOR DISPLAYING ULTRASONIC IMAGE

BACKGROUND OF THE INVENTION

FIELD OF THE INVENTION AND RELATED ART STATEMENT

The present invention relates to an apparatus for displaying ultrasonic images taken by an ultrasonic microscope in which a specimen is scanned two-dimensionally by a focused spot of an ultrasonic beam.

FIG. 1 shows a principal construction of a known ultrasonic microscope. A control unit 1 sends a control signal to a high frequency wave transmitting unit 2 to generate a high frequency burst signal in synchronism with the control signal. The high frequency burst signal generated from the transmitting unit 2 is supplied to a piezo electric transducer 4 via a circulator 3 and is converted into an ultrasonic wave. The ultrasonic wave is focused by an acoustic lens 5 an is projected via an ultrasonic wave propagating medium 6 such as water onto a specimen 7 as a fine spot. The ultrasonic wave thus projected upon the specimen 7 is reflected in accordance with acoustic characteristics of the specimen. The reflected ultrasonic wave is received by the acoustic lens 5 and is converted into an electric signal by the piezo electric transducer 4. The electric signal thus converted is supplied to a receiving unit 8 via the circulator 3. The electric signal is gated in the receiving unit 8 by means of a gate signal supplied from the control unit 1, so that unnecessary signals are removed from the electric signal. Then the electric signal thus gated is amplified and rectified to produce a rectified output signal having an amplitude representing a strength of the reflected ultrasonic wave. The rectified output signal thus obtained is supplied to a scan converter 11 to which are also supplied X and Y direction information signals relating to a scanning position on the specimen 7 and supplied from X direction scanner 9 and Y direction scanner 10, respectively. In the scan converter 11, the rectified output signal is stored as an amplitude signal. Then the amplitude signal is read out and converted into a video signal which is supplied to a display unit 12 such as a cathode ray tube monitor to display an ultrasonic image of the specimen. The X and Y direction scanners 9 and 10 are driven by control signals supplied from the control unit 1 and the acoustic lens 5 is vibrated in the X direction at a high speed by means of the X direction scanner 9 and a specimen table 13 is moved slowly in the Y direction by means of the Y direction scanner 10 so as to effect the two-dimensional scanning.

In the ultrasonic microscope explained above, a single ultrasonic image is obtained by scanning the specimen 7 within a given area, while a distance in the Z direction between the acoustic lens 5 and specimen 7 remains constant. Therefore, when the distance in the Z direction is successively changed in a stepwise manner, a plurality of ultrasonic images representing images of the specimen on different scanning planes at different depths are obtained successively. Therefore, when the ultrasonic lens 5 and specimen 7 are moved relatively to each other in the Z direction by a small pitch distance in a stepwise manner, there are obtained a large number of ultrasonic images and therefore, an inside construction of the specimen 7 can be inspected much more precisely and very small cracks can be found without fail.

Usually the ultrasonic image of the specimen is displayed on a monitor such as a cathode ray tube (CRT) or is recorded on a photographic film. Thus, when a resolution in the Z direction is increased by moving the acoustic lens and specimen relative to each other in the Z direction at a small pitch distance, there are obtained a large number of ultrasonic images. When the specimen is made of materials having uniform characteristics, similar ultrasonic images have to be compared with each other. This results in that small defects or cracks might not be detected. Particularly, in case of displaying ultrasonic images on a single CRT successively, only remarkable changes could be practically detected, because visual images are soon forgotten.

Contrary to this, in case of using the photographic records, it is possible to compare successive ultrasonic images in detail. However, since a great large number of photographic records have to be prepared, the running cost becomes expensive.

SUMMARY OF THE INVENTION

The present invention has for its object to provide a novel and useful apparatus for displaying ultrasonic images, said apparatus being able to avoid the drawbacks of the known apparatus and display a color ultrasonic image reconstructed from a plurality of ultrasonic images.

According to the invention, an apparatus for displaying ultrasonic images of a specimen picked-up by an ultrasonic microscope comprises an input port means for receiving a plurality of ultrasonic images successively supplied from the ultrasonic microscope;

a memory means for storing at least two ultrasonic images successively received at said input port means;

a means for reconstructing a color image from said at least two successive ultrasonic images stored in said memory means; and a display means for displaying said reconstructed color image.

BRIEF DESCRIPTION OF THE DRAWINGS

FIG. 5 is a schematic diagram explaining an operation of the displaying apparatus according to the invention.

DESCRIPTION OF THE PREFERRED EMBODIMENTS

Figure 2:
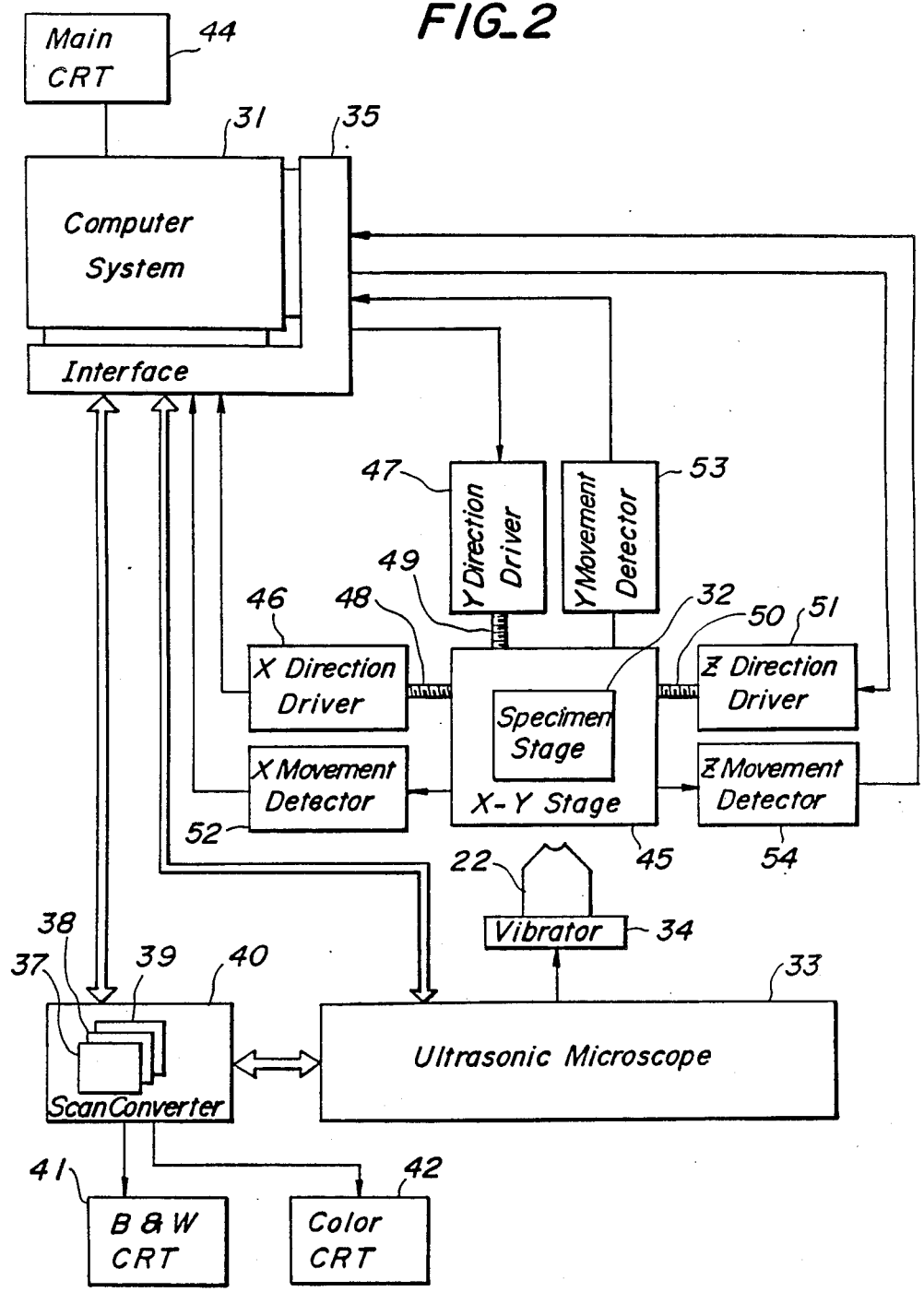
FIG. 2 is a block diagram showing an embodiment of the ultrasonic image displaying apparatus according to the invention.

FIG. 2 is a block diagram illustrating an embodiment of the displaying apparatus according to the invention. According to the invention, a plurality of ultrasonic images of a specimen taken at different depths are stored, and a false color image reconstructed from at least two successive stored ultrasonic images is displayed on a color display monitor.

Figure 1:
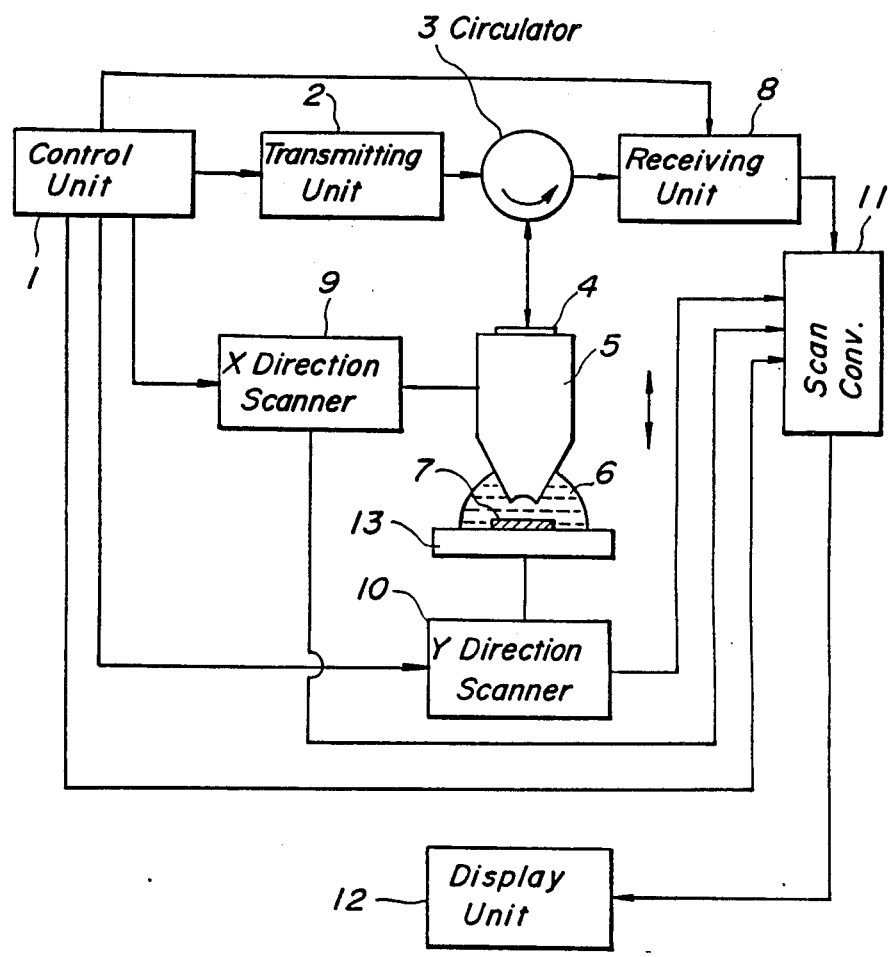
FIG. 1 is a block diagram showing an embodiment of a known ultrasonic microscope.

A reference numeral 33 denotes a main portion of an ultrasonic microscope and its construction is the same as that of the known ultrasonic microscope shown in FIG. 1 comprising high frequency transmitting unit, circulator, and receiving unit. A vibrator 34 for moving reciprocally an acoustic lens 22 in the X direction receives via an interface circuit 35 an X direction scanning signal supplied from a computer (hereinafter abbreviated as CPU) 31. The main portion of ultrasonic microscope 33 sends an electric signal obtained at the acoustic lens 22 to a scan converter 40 and is stored in three images memories 37, 38 and 39 successively. To the scan converter 40 are connected a black and white monitor (CRT) 41 and a color monitor 42.

The scan converter 40 functions to convert an amplutide of the received analog electric signal into a digital, signal composed of, for example, eight bits so as to obtain a gray scale of 256 steps and to store the digital signals in the image memories 37, 38 and 39. Any one of image signals stored in the image memories 37, 38, 39 can be displayed on the black and white monitor 41. Three ultrasonic images stored in the image memories 37, 38 and 39 may be obtained by moving the acoustic lens 22 toward or away from a specimen stage 32 in the Z direction at a given pitch or may be obtained by moving the speciment stage 32 in the XY plane while the distance between the acoustic lens 22 and specimen stage 32 in the Z direction remains constant. Each time an ultrasonic image of one frame has been taken, the image signals stored in the frame memories 37, 38 and 39 are renewed by succeeding image signals. That is to say, when first, second and third ultrasonic images have been stored in the image memories 37, 38 and 39, respectively, a fourth ultrasonic image is newly stored in the image memory 39, and the second and third images stored in the image memories 38 and 39 are transferred to the image memories 37 and 38, respectively. The scan converter 40 further functions to reconstruct a color image from the three ultrasonic images stored in the image memories 37, 38 and 39, and to display the color image thus reconstructed on the color CRT 42 under the control of CPU 31.

A reference numeral 45 denotes an X-Y stage supporting the specimen stage 32, and the X-Y stage is coupled with X and Y direction driving means 46 and 47 via shafts 48 and 49, respectively. The X-Y stage 45 is further coupled with a Z direction driving means 51 by means of a shaft 50 so that the X-Y stage 45 is moved in the Z direction. It should be noted that the acoustic lens 22 instead of the X-Y stage 45 may be moved in the Z direction. The X, Y and Z driving means 46, 47 and 51 are controlled by driving signals supplied from the CPU 31 to drive the X-Y stage 45 in a desired manner. Amounts of movement of the X-Y stage 45 in the X, Y and Z directions are detected by X, Y and Z direction movement amount detecting means 52, 53 and 54 comprising encoders for detecting rotating pulses for motors provided in the driving means. The signals thus detected are supplied to the CPU 31 via the interface circuit 35. To the CPU 31 is further connected a main CRT 44 for displaying input commands, operation commands, etc.

Figure 3:
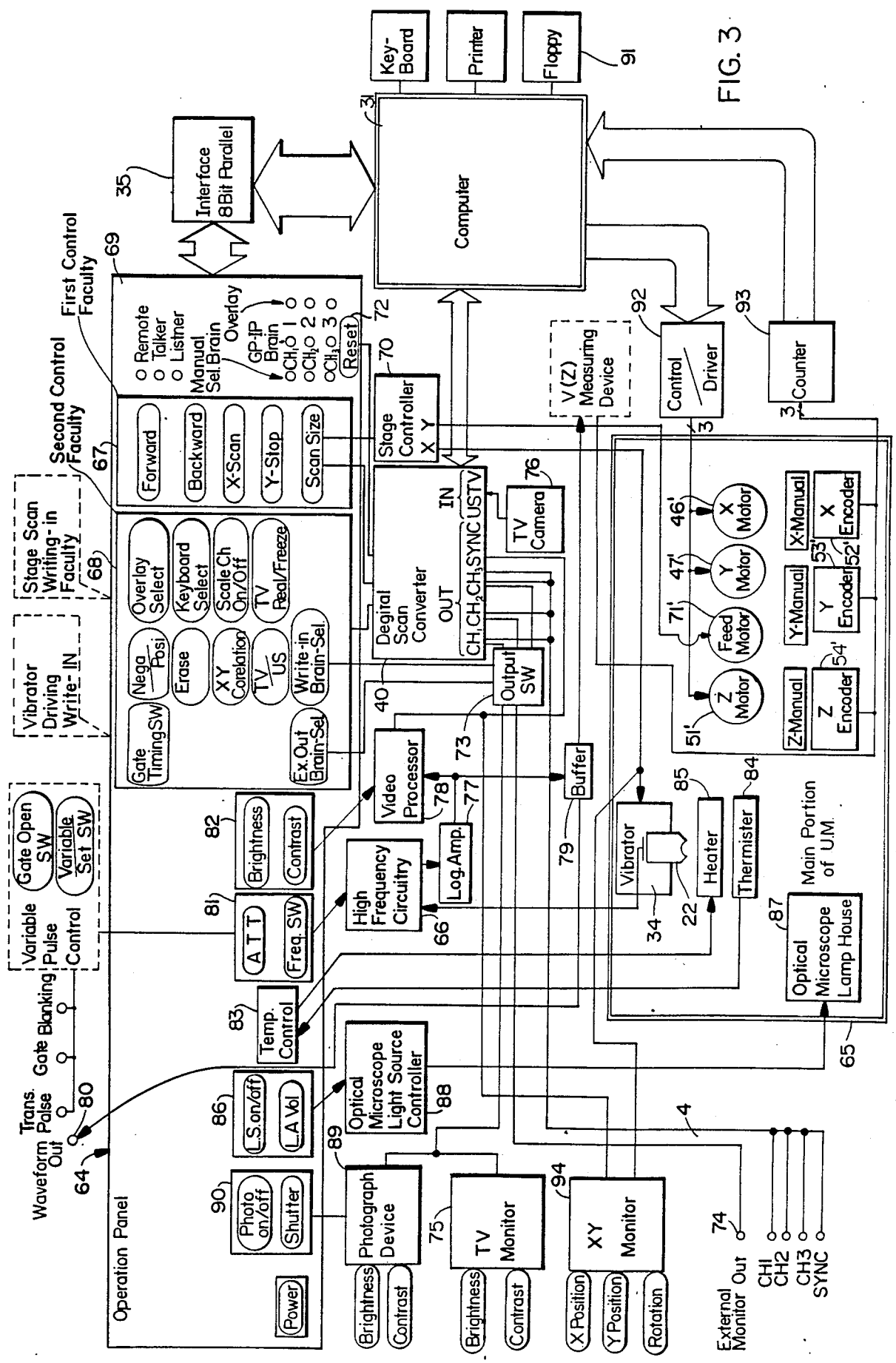
FIG. 3 is a block diagram showing an ultrasonic microscope comprising the displaying apparatus according to the invention.

FIG. 3 is a block diagram showing the whole construction of the ultrasonic microscope including the displaying apparatus according to the invention except for the monitors. In FIG. 3, reference numeral 64 represents an input device, i.e. operation panel, 65 a main portion of the ultrasonic microscope 33 and reference numeral 66 denotes a high frequency circuitry 66 including the transmitting and receiving units. In FIG. 3, portions similar to those illustrated in FIG. 2 are denoted by the same reference numerals used in FIG. 2.

The input device 64 comprises first group control faculty 67, second group control faculty 68 and light emitting diode group 69 for displaying various operation modes. The first group control faculty 67 corresponds to switches and monitor elements provided in a first area 101 of a front panel shown in FIG. 4A, and the second group control faculty 68 can be performed by a set of switches provided in a second area 102 of the front panel.

The first group control faculty 67 is connected to scan converter 40 and stage controller 70 and effects ultrasonic image write-in start switching (forward and backward), X direction scan switching, Y direction scan stop and scan width switching. The X and Y scan driving signals are supplied from the stage controller 70 to vibrator 34 and Y direction driving motor 71, respectively. To the scan converter 40 is further connected a D.S.C. (digital scan converter) reset switch faculty 72. The digital scan converter 40 includes three image memories 37, 38 and 39 and three channel output ports CH1, CH2 and CH3 related to the image memories 37, 38 and 39, respectively. The channel output ports CH1, CH2 and CH3 are then connectable via an output switch circuit 73 to external monitor output terminal 74 and television monitor 75. The television monitor 75 is placed in front of a photograph pick-up device 89 so that photographic records of ultrasonic images can be taken in a usual manner.

It should be noted that the output terminals CH1, CH2 and CH3 and synchronizing signal output terminal SYNC of the scan converter 40 may be connected to the color CRT 42 shown in FIG. 2. Further, a television camera 76 is connected to the scan converter 40.

An electric signal from the acoustic lens 22 is supplied to an ultrasonic image input terminal US of the scan converter 40 by means of high frequency circuit unit 66, log-amplifier 77 and video signal processing circuit 78. An output signal from the log-amplifier 77 is supplied through a buffer amplifier 79 to a signal output terminal 80 so that a signal waveform may be monitored.

The second group control faculty 68 includes polarity changeover switching (NEGA/POSI), image erasing (ERASE), XY corelation switching (on and off of smoothing process), TV/US changeover, overlay selection (switching of overlay memory for displaying character information from CPU 31), keyboard character output selection switching, scale character on/off switching, TV real/freeze (storing of TV camera signal), external monitor output changeover switching, gate timing changeover switching, etc. By controlling the output changeover circuit 73, it is possible to effect write-in blain selection and partial output blain selection for the image memories 37, 38 and 39.

REMOTE LED is lighted on when the scan converter 40 is controlled by CPU 31, TALKER LED is activated when the contents stored in the image memories of the scan converter 40 are transferred to CPU 31 and LISTNER LED is lighted on when the signal is written-in. Further, GP-IB access channel display LED indicates the channel of the scan converter 40 which is accessed by CPU 31, and GP-IB access overlay memory LED represents an overlay memory of the scan converter 40 which is accessed by CPU 31.

A reference numeral 81 represents attenuation amount and frequency changeover faculty, 82 control faculty for the processing circuit 78, and 83 represents temperature control faculty for the specimen stage 32, to the temperature control faculty being connected thermistor 84 and heater 85. A reference numeral 86 denotes control faculty for an optical microscope 87 and connected to a light source controller 88 which controls a brightness of illumination light for the optical microscope 87. Further, a reference numeral 90 indicates a control faculty 90 for the photograph pick-up device 89. The CPU 31 is connected to a floppy device 91 so that various kinds of image processings and inclination adjustments can be performed.

Reference numerals 46', 47' and 51' denote stepping motors provided in the X, Y and Z direction driving means 46, 47 and 51, and 52', 53' and 54' represent encoders of the X, Y and Z direction movement amount detecting means 52, 53 and 54. The stepping motors 46', 47' and 51' are driven by a control/driver 92 controlled by CPU 31, and output signals from the encoders 52', 53' and 54' are entered into CPU 31 via a counter 93.

Figure 4A:
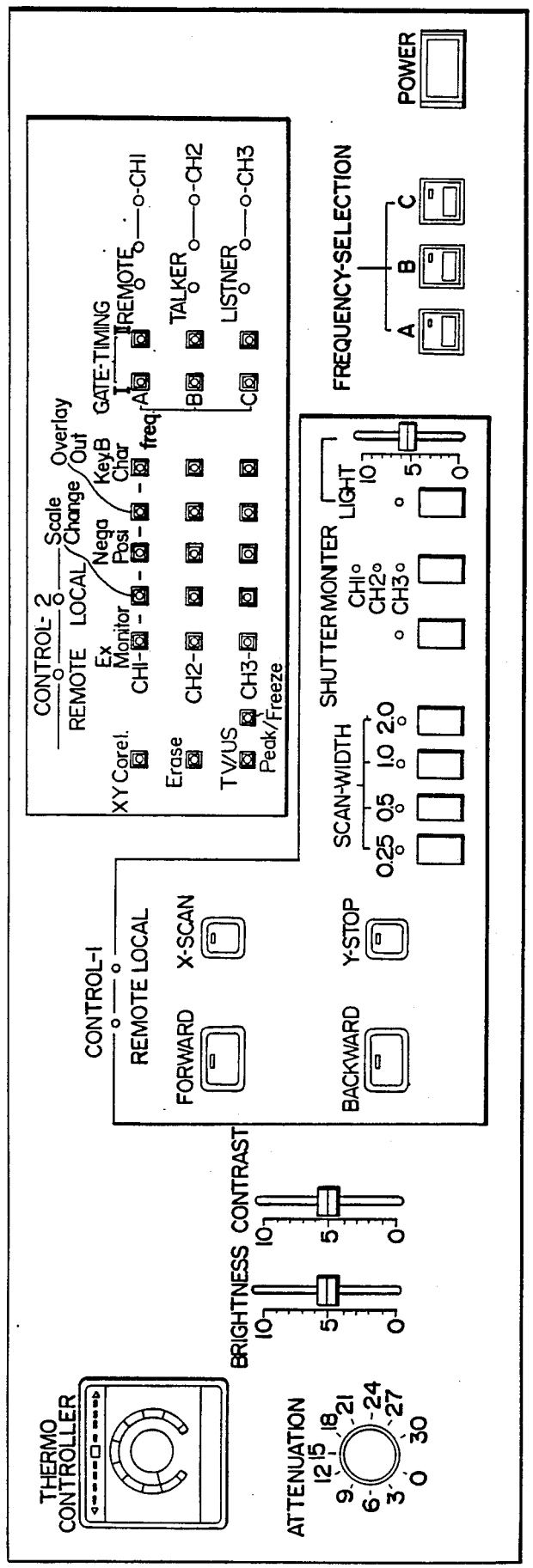
FIGS. 4A and 4B are plan views showing panels of the ultrasonic microscope shown in FIG. 2.
Figure 4B:
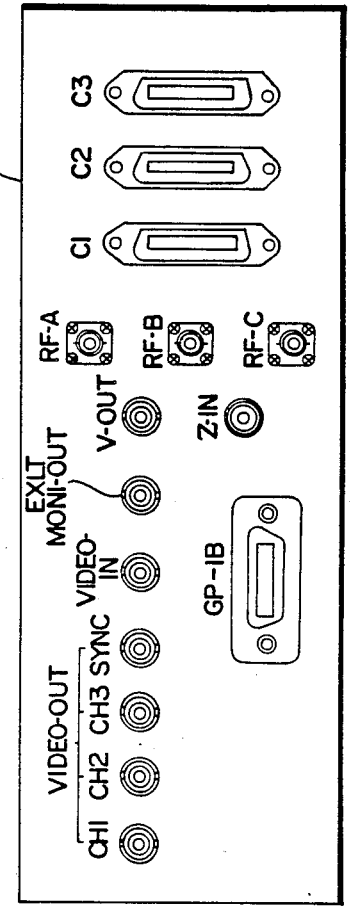

FIG. 4A illustrates a construction of the front panel and FIG. 4B shows a construction of the rear panel. As shown in FIG. 4B, the rear panel 103 comprises output terminals (VIDEO-OUT) for channels CH1, CH2 and CH3, synchronizing signal output terminal (SYNC), GP-IB connector, video input terminal (VIDEO-IN), a video output terminal (EXIT.MONI-OUT), V-OUT, Z-IN, RF-A, RF-B, RF-C and C1, C2 and C3 connectors for keyboard, printer and floppy device.

Now the operation of the displaying apparatus according to the invention will be explained also with reference to FIG. 5.

FIG. 5 is a schematic diagram for explaining the operation of 3Z-mode color display in which a color image signal is reconstructed from three successive ultrasonic images obtained by moving the acoustic lens 22 in the Z direction toward the specimen at a given pitch. When the amount Z of movement of the acoustic lens 22 is zero (Z=0), a first ultrasonic image is picked-up and stored in the image memory 39 of the scan converter 40. Then after the acoustic lens 22 has been moved in the Z direction by a distance $Z=Z_1$, a second ultrasonic image is picked-up and stored in the image memory 39. The first ultrasonic image stored in this image memory 39 is transferred into the image memory 38. Furhter the acoustic lens 22 is moved in the Z direction by a distance $Z_2$ to store a third ultrasonic image in the image memory 39. In this case, the first and second ultrasonic images are transferred into the image memories 37 and 38, respectively. In this manner, the successive three ultrasonic images have been stored in the image memories 37, 38 and 39. Then the image signals thus stored in the image memories 37, 38 and 39 are simultaneously read out at the video output terminals CH1, CH2 and CH3, respectively together with the synchronizing signal supplied to the output terminal SYNC. The first, second and third video output terminals serve to supply red, green and blue color signals, respectively, so that a color image reconstructed from the three successive ultrasonic images can be displayed on the color monitor 42. Then internal defects which could not be inspected on the surface of the specimen are displayed by colors and therefore, the defects can be easily and positively inspected. Moreover, in the present embodiment, since successive three ultrasonic images are always stored in the image memories, they can be compared with each other and fine impurities and cracks can be detected easily.

As explained above in detail, in the displaying apparatus according to the invention, a plurality of ultrasonic images successively taken by the ultrasonic microscope can be displayed successively and, at the same time, a color image reconstructed from these successive ultrasonic images is displayed on the color display device. Therefore, any defects such as fine impurities and cracks within the specimen can be detected easily and positively.

What is claimed is:

1. An apparatus for displaying ultrasonic images of a specimen picked-up by an ultrasonic microscope comprising:
    means for focusing an ultrasonic beam of an ultrasonic microscope to a focal point;
    means for detecting a position of said focal point with respect to a specimen, and for generating respective X, Y and Z positional signals indicative of said detected position;
    input port means for receiving a plurality of ultrasonic images successively supplied from the ultrasonic microscope;
    memory means for storing at least two ultrasonic images successively received at said input port means, in respective image memories;
    means for writing each of said at least two ultrasonic images into said memory means, comprising means for selecting one of said image memories under control of said Z positional signal, and means for selecting a storage position within said selected image memory under control of said X and Y positional signals;
    means for reconstructing a color image from said at least two successive ultrasonic images stored in said memory means; and
    display means for displaying said reconstructed color image.

2. An apparatus according to claim 1, wherein said memory means comprises three image memories for storing three ultrasonic images successively received at the input port means, and said reconstructing means reconstructs a color image composed of red, green and blue color signals respectively corresponding to said three ultrasonic images.

3. An apparatus according to claim 1, further comprising means for displaying at least one of said plurality of ultrasonic images stored in said memory means.

4. An apparatus according to claim 1, wherein said plurality of ultrasonic images are picked-up by varying said distance between a specimen and an acoustic lens in the Z direction.

5. An apparatus according to claim 1, wherein each of said plurality of ultrasonic images are picked-up by moving a specimen, relative to an acoustic lens of said ultrasonic microscope, in the XY plane.

6. An apparatus according to claim 1, wherein said memory means comprises a plurality of digital image memories and a color image is reconstructed by reading out simultaneously corresponding positions of the digital image memories as different color signals.

* * * * *